(12) United States Patent
Lee et al.

(10) Patent No.: US 12,014,805 B2
(45) Date of Patent: *Jun. 18, 2024

(54) HEALTH TRACKING SYSTEM WITH MEAL GOALS

(71) Applicant: MYFITNESSPAL, INC., San Francisco, CA (US)

(72) Inventors: Chul Lee, San Francisco, CA (US); Angela Hsiao, San Francisco, CA (US)

(73) Assignee: MyFitnessPal, Inc., Austin, TX (US)

( * ) Notice: Subject to any disclaimer, the term of this patent is extended or adjusted under 35 U.S.C. 154(b) by 17 days.

This patent is subject to a terminal disclaimer.

(21) Appl. No.: 17/552,867

(22) Filed: Dec. 16, 2021

(65) Prior Publication Data

US 2022/0108776 A1 Apr. 7, 2022

Related U.S. Application Data

(63) Continuation of application No. 15/241,129, filed on Aug. 19, 2016, now Pat. No. 11,227,673.

(51) Int. Cl.
| | |
|---|---|
| *G16H 10/20* | (2018.01) |
| *G16H 10/60* | (2018.01) |
| *G16H 20/60* | (2018.01) |
| *G16H 40/63* | (2018.01) |
| *G16H 50/30* | (2018.01) |

(52) U.S. Cl.
CPC ............. *G16H 10/20* (2018.01); *G16H 10/60* (2018.01); *G16H 20/60* (2018.01); *G16H 40/63* (2018.01); *G16H 50/30* (2018.01)

(58) Field of Classification Search
CPC ........ G16H 10/20; G16H 10/60; G16H 20/60; G16H 40/63; G16H 50/30
See application file for complete search history.

(56) References Cited

U.S. PATENT DOCUMENTS

| 8,690,578 | B1 | 4/2014 | Nusbaum et al. |
| 2010/0136508 | A1 | 6/2010 | Zekhtser |
| 2011/0218407 | A1 | 9/2011 | Haberman |
| 2011/0318717 | A1 | 12/2011 | Adamowicz |
| 2017/0039886 | A1* | 2/2017 | Bitran ................ G09B 19/0092 |

\* cited by examiner

*Primary Examiner* — Robert A Sorey
*Assistant Examiner* — Kimberly A. Sass
(74) *Attorney, Agent, or Firm* — Maginot, Moore & Beck, LLP

(57) ABSTRACT

Apparatus and methods for deriving a dietary plan. In one embodiment, the method comprises enabling a user to enter a long-term dietary goal at a health tracking device; accessing user profile information relating to the user; generating at least one value representative of a short-term dietary goal for the user based at least in part on the long-term dietary goal and the user profile information; dividing the at least one value of the short-term dietary goal among a plurality of dietary portions; and enabling the user to adjust the relative amount of the at least one value apportioned to each of the plurality of dietary portions.

5 Claims, 9 Drawing Sheets

410
Receive user data including at least one long term dietary goal.

420
Generate daily dietary goals for the user based on the received long term dietary goal for the user.

430
Obtain meal goal for the user.

440
Generate meal guidelines for the user based on the received meal goal for the user.

HEALTH TRACKING SYSTEM WITH MEAL GOALS

CROSS-REFERENCE TO RELATED APPLICATIONS

This application is a continuation of U.S. patent application Ser. No. 15/241,129, filed Aug. 19, 2016, the entire contents of which are incorporated by reference herein.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The method and system disclosed in this document relate to health and fitness tracking devices and, more particularly, to devices configured to collect and display nutritional information and define user goals associated therewith.

BACKGROUND

Health and fitness tracking devices are increasingly utilized by individuals interested in tracking metrics related to their personal health and fitness. Some health and fitness tracking devices allow user to enter foods and beverages consumed by the user. In response to the foods and beverages entered by the user the health and fitness tracking devices provide the user with associated data concerning calorie consumption and nutritional intake. This data may be used to assist the user in meeting various goals related to weight loss, sugar intake limits, proper nutrition, or any of various other healthy lifestyle goals.

Challenges exist with user goals in health tracking systems. In particular, for users with long-term goals it is often difficult for these users to determine what daily behaviors will be best in helping the user achieve the desired goal. For example, for a user wishing to lose ten pounds in a month, it may be difficult for the user to which set of activities and/or meals in a given day will best assist the user in achieving the desired goal. Furthermore, even if the user has a plan to achieve the goal, the user may not understand the impact of straying from the plan or how to get back on course toward achieving the desired goal.

In view of the foregoing, it would be advantageous to provide a health tracking system and related method that allows users achieve a desired larger goal via utilization of a series of smaller goals. It would also be advantageous if such a health tracking system enabled the user to more easily understand the impact of daily decisions on the plan for achieving the desired long-term goal. Moreover, it would be advantageous if such a health tracking system could provide tools and resources to help a user who strays from smaller goals to get back on course toward achieving the desired larger goal.

SUMMARY

In accordance with one exemplary embodiment of the disclosure, a method of providing guidelines for a user of a health tracking device is disclosed. In one embodiment, the method comprises: enabling a user to enter a long-term dietary goal at a health tracking device; accessing user profile information relating to the user; generating at least one value representative of a short-term dietary goal for the user based at least in part on the long-term dietary goal and the user profile information; dividing the at least one value of the short-term dietary goal among a plurality of dietary portions; and enabling the user to adjust the relative amount of the at least one value apportioned to each of the plurality of dietary portions.

In another exemplary embodiment, the method comprises: providing an interface to enable a user to enter a long-term nutrition or weight-related goal; utilizing user profile information to identify a daily caloric value necessary to achieve the long-term nutrition or weight-related goal; automatically apportioning the daily caloric value across a plurality of individual meals associated with each day; and enabling the user to dynamically adjust the portion of the daily caloric value apportioned to each of the plurality of individual meals.

In accordance with one exemplary embodiment of the disclosure, a non-transitory computer-readable medium for operating a health tracking system is disclosed. In one embodiment, the computer-readable medium comprises a plurality of instructions stored thereon that, when executed by a processor, cause the processor to: receive at least one long-term dietary goal generate at least one short-term dietary goal for a user based at least in part on the at least one long-term dietary goal and user profile data, the short-term dietary goal being comprised of one or more individual meals; appropriate a portion of the short-term dietary goal as a sub-goal for each of the one or more individual meals, the sub-goals comprising values for one or more nutrition-related aspects receive data relating to one or more consumed items associated to a first one of said one or more individual meals, the data comprising values for the one or more nutrition-related aspects; and update the sub-goals for subsequent ones of the one or more individual meals based on a difference between the values of the one or more nutrition-related aspects of the received data and the short-term goal values.

The above described features and advantages, as well as others, will become more readily apparent to those of ordinary skill in the art by reference to the following detailed description and accompanying drawings. While it would be desirable to provide a health tracking system that provides one or more of these or other advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

The foregoing aspects and other features of a health and fitness tracking system are explained in the following description, taken in connection with the accompanying drawings.

Figure 1:
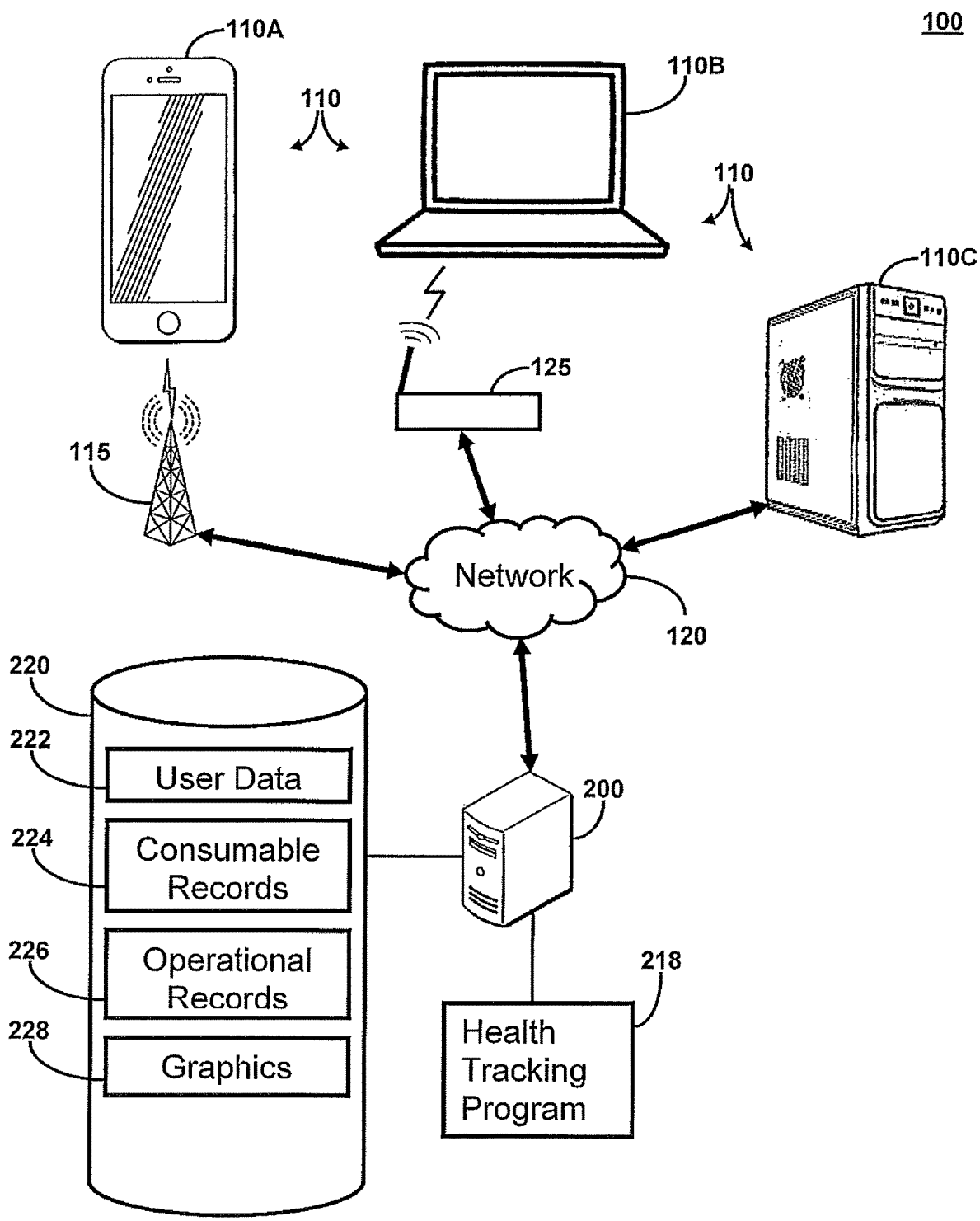
FIG. 1 shows a block diagram illustrating a health tracking system in accordance with the present disclosure.

All Figures © MyFitnessPal, Inc. 2021. All rights reserved.

DETAILED DESCRIPTION

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Disclosed embodiments include systems, apparatus, and methods associated with health and fitness tracking in general, and in particular a system configured to define and dynamically adjust meal goals.

Aspects of the disclosure are disclosed in the accompanying description. Alternate embodiments of the present disclosure and their equivalents may be devised without parting from the spirit or scope of the present disclosure. It is noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art will readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description is not to be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As used herein, the term "consumable" refers to foods, beverages, dietary supplements, vitamin supplements, medication, or other items for consumption. As used herein, the phrases "consumable record" and "consumable data record" refers to a data record comprising information relating to a particular consumable item. Each consumable record comprises a plurality of data fields that relate to a particular consumable. In some embodiments, the consumable record includes a description field that includes data, such as a text string, that identifies or describes the particular consumable. In some embodiments, each consumable record includes fields for caloric content, macronutrients, micronutrients, serving size, and other nutrition and health information.

Health Tracking System

With reference to FIG. 1, an exemplary embodiment of a health tracking system 100 configured to define and dynamically adjust meal guidelines is shown. In the illustrated embodiment, the health tracking system 100 includes a plurality of health tracking devices 110 in communication with a system server 200 or other data processing system via a network 120 such as, e.g. the Internet.

As will be explained in further detail herein, the system server 200 is in communication with a database 220 configured to store user data 222 and a plurality of consumable records 224. The system server 200 is configured to generate daily dietary goals for the user, and then generate and/or receive at least one meal goal from the health tracking device based on the generated daily dietary goals. In a further embodiment, the system server 200 is further configured to generate individual meal guidelines for the user based at least in part on the meal goals received and/or the generated daily dietary goals.

The server 200 comprises a computerized device or data processing system configured to run one or more software applications on a processor thereof (e.g. the network-side health tracking program 218). The server 200 of the present embodiment includes an interface 210 configured to receive user data from the health tracking devices 110. The user data includes user profile data, user goals, and data related to consumable items consumed by users of the health tracking system 100. The user data is stored in a database 220 provided in a storage apparatus or memory accessible by the server 200. The database 220 includes user data 222, consumable records 224, operational records 226, and graphics 228. The database 220 may be retained within the server 200 and included on the data store or other memory of the server. Alternatively, in lieu of the database 220 being commonly housed with the server 200, the database 220 may be located at a remote location from the server at a separate storage entity (not shown), and the server 200 may be in communication with the separate storage entity.

In addition to storing data, the memory of the server 200 is further configured to store instructions including a network-side health tracking program 218 (which may also be referred to herein as the "health tracking application"). The database 220 is accessible by at least the health tracking program 218. As explained in further detail below, the health tracking program 218 is configured to be executed by a processor 204 of the server 200, and generate daily dietary goals for the user. The health tracking program 218 is further configured to generate meal guidelines for the user and dynamically update such meal guidelines based on the user data, as discussed elsewhere herein.

With continued reference to FIG. 1, the server 200 is in communication with the health tracking devices 110 via a network 120. The health tracking devices 110 (which may also be referred to herein as "health and fitness tracking devices" and/or "user devices") comprise any number of computerized apparatus such as e.g., a smartphone 110A, laptop computer 110B, a tablet computer, a desktop computer 110C, or other such device. As demonstrated in the exemplary user device 110 of FIG. 3, each health tracking device 110 includes a user interface 304. In at least one embodiment, the user interface 304 may comprise an LCD touch screen or the like, a mouse or other pointing device, a keyboard or other keypad, speakers, and a microphone, as will be recognized by those of ordinary skill in the art. The user interface 304 allows the user to input user data and also, and also provides the user with any of various health, fitness and activity related data such as food and nutritional consumption, calorie expenditure, sleep metrics, weight, body fat, heart rate, distance travelled, steps taken, etc. such as via a display screen 302.

In order to connect to the network 120, as demonstrated in FIG. 1, the health tracking devices 110 are generally configured to utilize any of various wired or wireless communications components, infrastructures and systems, such as cell towers 115 of a mobile telephony network, wireless routers 125, Bluetooth®, near field communication (NFC), or physical cables. Health tracking devices 110 may use data collected from sensors associated to or in communication with the health tracking device 110, such as heart rate monitors, step counters, stair counters, global positioning system ("GPS") tracking devices, as well as various other motion tracking and biometric monitoring devices; alternatively, or in addition, a user may manually enter health related data. Such sensors allow the user to easily track and automatically log activity and/or consumption information with the user device 110.

The health tracking devices 110 are configured to communicate with the system server 200 in order to enable: entry of user data 222, accessing and searching of the consumable records 224 stored in the database 220, display of the consumable records 224 on the health tracking devices 110, display of additional records, and/or selection of individual ones of the displayed consumable records for the purposes of caloric and nutritional logging. In one embodiment, foregoing functions are performed via execution of one or more software applications at the server 200 (i.e., server or network-side applications) in communication with one or more complementary software applications at the health tracking devices 110 (i.e., client-side applications). For example, the health tracking program 218, running on the processor 204 may be utilized to accomplish the foregoing, as explained in further detail below. Alternatively, or in addition, a client-side software application for performing various functions necessary for the concept disclosed herein may also be utilized (e.g., see the health tracking application 318 of the smartphone 110A of FIG. 3, discussed below). Accordingly, it will be recognized that any of various processing described herein as being performed at the server 200 may alternatively be provided on a health tracking device, and vice-versa, in order to accomplish the desired functionality of the health tracking system 100, as described herein.

System Server

Figure 2:
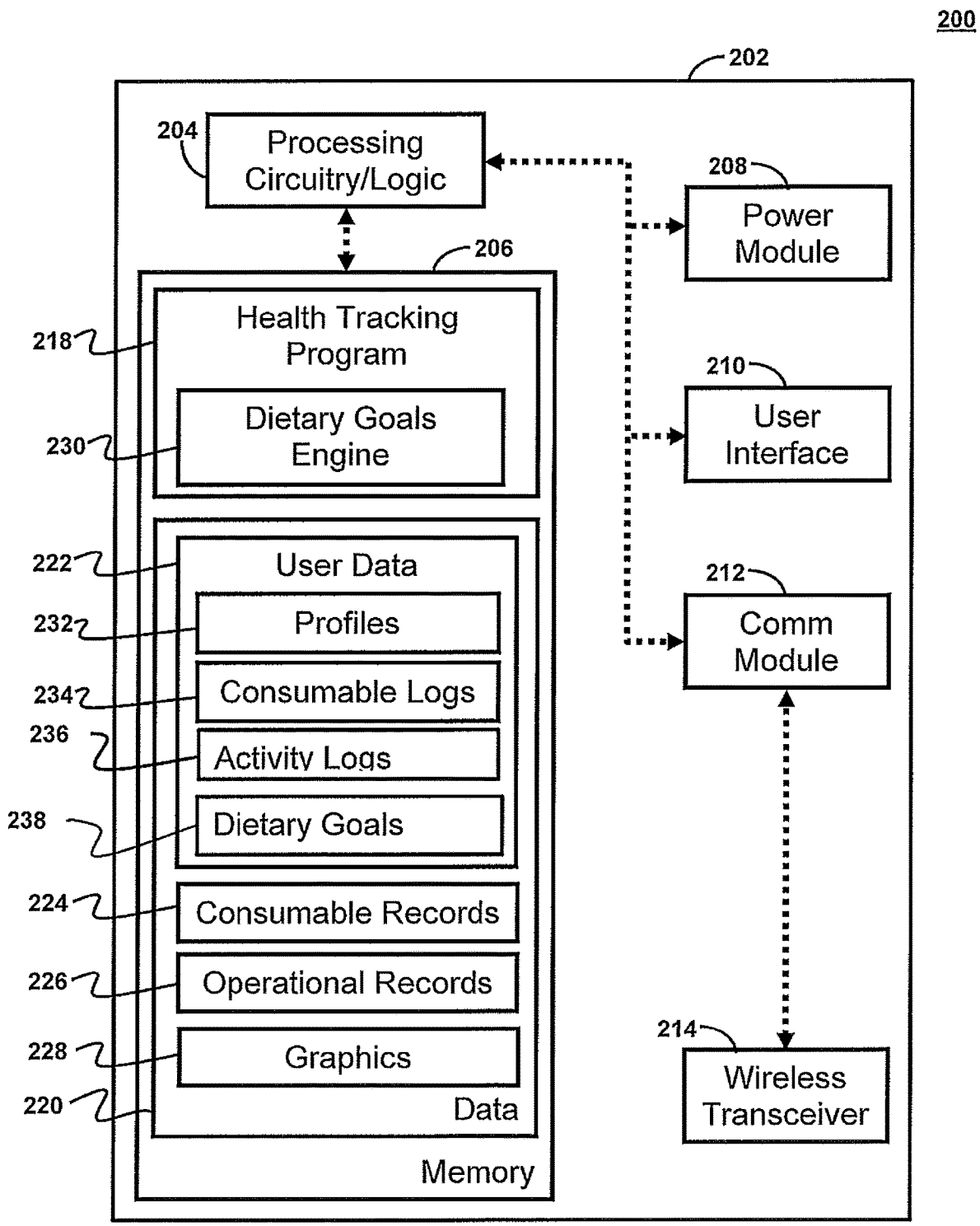
FIG. 2 shows a block diagram illustrating an exemplary smartphone of the health tracking system of FIG. 1.

With reference now to FIG. 2, a block diagram of an exemplary embodiment of the system server 200 of FIG. 1 is shown. It is appreciated that the embodiment of the system server 200 shown in FIG. 2 is only one exemplary embodiment of a system server 200. As such, the exemplary embodiment of the system server 200 of FIG. 2 is merely representative of any of various manners or configurations of system servers or other data processing systems that are operative in the manner set forth herein.

The system server 200 of FIG. 2 is typically provided in a housing, cabinet or the like 202 that is configured in a typical manner for a server or related computing device. In one embodiment, the system server 200 includes processing circuitry/logic 204, memory 206, a power module 208, a user interface 210, a network interface in the form of a network communications module 212, and a wireless transceiver 214.

The processing circuitry/logic 204 is operative, configured and/or adapted to operate the system server 200 including the features, functionality, characteristics and/or the like as described herein. To this end, the processing circuitry/logic 204 is operably connected to the memory 206, the power module 208, the user interface 210, the network communications module 212, and the wireless transceiver 214. The memory 206 may be of any type of device capable of storing information accessible by the processor 204, such as a memory card, ROM, RAM, write-capable memories, read-only memories, hard drives, discs, flash memory, or any of various other computer-readable medium serving as data storage devices as will be recognized by those of ordinary skill in the art. The memory 206 is configured to store instructions including a network-side health tracking application 218 for execution by the processing circuitry/logic 204, as well as a database 220 for use by at least the health tracking program 218. The database 220 includes user data 222, consumable records 224, operational records 226, and graphics 228. As discussed in greater detail below, the health tracking application 218 includes a dietary goals engine 230 configured to evaluate user goals and other user data and generate daily dietary goals as well as meal guidelines.

With continued reference to FIG. 2, the power module 208 of the system server 200 is operative, adapted and/or configured to supply appropriate electricity to the system server 200 (i.e., including the various components of the system server 200). The power module 208 may operate on standard 120 volt AC electricity, but may alternatively operate on other AC voltages or include DC power supplied by a battery or batteries.

The network communication module 212 of the system server 200 provides an interface that allows for communication with any of various devices using various means. In particular, the network communications module 212 includes a local area network port that allows for communication with any of various local computers housed in the same or a nearby facility. In some embodiments, the network communications module 212 further includes a wide area network port that allows for communications with remote computers over the Internet (e.g., network 120 of FIG. 1). Alternatively, the system server 200 communicates with the network 120 via a modem and/or router of the local area network. In one embodiment, the network communications module is equipped with a Wi-Fi transceiver 214 or other wireless communications device. Accordingly, it will be appreciated that communications with the system server 200 may occur via wired communications or via the wireless communications. Communications may be accomplished using any of various known communications protocols. In the embodiment of FIG. 2, the wireless transceiver 214 may be a Wi-Fi transceiver, but it will be recognized that the wireless transceiver may alternatively use a different communications protocol.

The system server 200 may be accessed locally by an authorized user (i.e., an administrator or operator). To facilitate local access, the system server 200 includes an interactive user interface 210. The health tracking application 218 may collect data from and store data to the memory 206. In at least one embodiment, the user interface 210 may suitably include an LCD touch screen or the like, a mouse or other pointing device, a keyboard or other keypad, speakers, and a microphone, as will be recognized by those of ordinary skill in the art. Accordingly, the user interface 210 is configured to provide an administrator or other authorized user with access to the memory 206 and allow the authorized user to amend, manipulate and/or display information contained within the memory.

As mentioned previously, the memory 206 includes various programs and other instructions that may be executed by the processor circuitry/logic 204. In particular, the memory 206 of the system server 200 of FIG. 2 includes the health tracking program 218 (which may also be referred to herein as a "health tracking application" and/or the "network-side health tracking application"). The health tracking program 218 is configured to cause the system server 200 receive user data from a user and provide nutritional data to the user related to any of various consumables. Execution of the health tracking application 218 by the processor circuitry/logic 204 results in signals being sent to and received from the user interface 210 and/or to the communications module 212 (for further delivery to a user device such as a health tracking device 110), in order to allow the user receive and update various aspects of the user data 222 and/or the consumable records 224. The network-side health tracking application 218 is further configured to provide various graphical views and screen arrangements to be displayed to a user on a user device 110.

The user data 222 includes at least user profiles 232, corresponding consumable logs 234, activity logs 236, and dietary goals 238. The user profiles 232 include a profile data for each user of the health tracking system 100. Each user profile includes demographic information for the users such as name, age, gender, height, weight, performance or activity level (e.g., beginner, intermediate, professional, sedentary, active, etc.) and/or other information for the user. The performance level may be determined based on an amount and/or frequency of recorded activity. For example, users who log several hours of workouts per week may be deemed "active" while those that record less than 2 hours per week are deemed "sedentary", etc. In other embodiments, rather than a systematic or automatic determination of the user's activity or performance level, the user him/herself may enter the information based on a subjective view of his/her lifestyle. The user profile data may also include one or more goals. The user's goals may be provided as any number of different types of goals, such as activity goals, dietary goals, weight-loss goals, or any of various other health-related goals. The user goals may be long-term or short term goals. For example, one user goal may be to lose twenty-five pounds within a year. Another user goal may be to limit calorie consumption at breakfast to 400 total calories per day. Yet another exemplary user goal may be to eat a minimum of 100 grams of protein per day. The user goals may also be general or specific goals. For example, one user may define a specific amount of weight as a weight-loss goal. Another user may more generally define a "healthy-lifestyle," "vegetarian diet," or "muscle building" as a goal.

In at least one embodiment, the consumable logs 234 include a consumable diary/log for each user. The consumable diary/log allows the user to track consumables that are consumed by the user over a period of days, weeks, months, etc., and any nutritional data associated with the food consumed. For example, the consumable diary/log may allow the user to enter, via a user device 110, particular consumable that is consumed by the user and have that data stored so that the user may keep track of the associated calories, macronutrients, micronutrients, sugar, fiber, and/or any of various other nutritional data associated with the consumables entered by the user in the consumable diary/log. The consumable logs 234 include a plurality of consumable records 224 entered by the user via the health tracking device 110, each of the consumable records is associated with a day of consumption and may also include a time or event associated with the consumption (e.g., breakfast, lunch, dinner, snack, etc.). The term "consumption data" as used herein refers to data in the consumable logs 234 that has been logged by the user and is associated with a particular day.

The activity logs 236 include various activity and fitness data which is either manually entered or automatically collected by sensors (not shown) associated with the health tracking devices 110. The sensors may be, for example, GPS devices, accelerometers, heart rate monitors, temperature sensors, etc. The activity logs 236 may indicate any of various activity-related parameters such as step count, heart rate, distance travelled, calories burned, etc. The activity logs 236 provide a diary/log of health and fitness data for a user that extends over some period of time, such as days, week, months, years, etc.

The dietary goals 238 are generated by the dietary goals engine 230 of the health tracking program 218. The dietary goals 238 provide each user with consumption recommendations that, if followed, will allow the user to achieve the user-defined goals as set forth in the user data. The dietary goals 238 may be related to any of various health-related parameters, including calorie or nutritional intake. The dietary goals may apply to some period of time, including longer periods of time (e.g., a week) or shorter periods of time (e.g., a day or a meal), or may continue indefinitely. For example, the dietary goals 238 may indicate that a user with a particular weight-loss goal should limit total calories for a day to less than some threshold number (e.g., 1700 calories per day, or 500 calories for a particular meal). As another example, the dietary goals may indicate that a user with a healthy-lifestyle goal should consume a minimum amount of vitamin C in a week, with this minimum vitamin C intake to continue as long as the user retains the healthy lifestyle goal.

With continued reference to FIG. 2, in addition to the user data 222, the data stored in the memory 206 also includes consumable records 224, operational records 226, and graphics 228. As discussed above, the phrase "consumable record" refers to a database record comprising information that relates to a particular consumable item. In at least one embodiment, each consumable record comprises a plurality of data fields that related to a particular consumable item. In the disclosed embodiment, each of the consumable records includes a number of fields including, for example, a name for the consumable item, summary information about the consumable item, and detailed nutritional information about the consumable item. Detailed information about a consumable may include one or more of: serving size, calories, ingredients, or any other nutritional information about the consumable item. For example, the nutritional information may include information that may be provided on USDA food labels or state-regulated food labels (e.g., vitamin and mineral content, fat content, cholesterol content, protein content, sugar content, carbohydrate content, fiber content, organic contents, etc.). The summary information about the consumable item may include a subset of the detailed information listed above. For example, the summary information about the consumable may only include serving size and calorie information. The various fields of each consumable record may be populated by data from any user or third party data providers. Therefore, it will be recognized that in at least some embodiments, consumable records 224 may have been entered by any of various sources including an administrator or operator of the health tracking system 100, commercial food providers (e.g., food distributors, restaurant owners, etc.), and/or users of the health tracking system 100.

The operational records 226 include current and historical data stored by the system server 200 in association with operation of the system server 200, execution of the health tracking application 218, and/or manipulation of data 220 within the memory 206. For example, the operational records 226 may include information concerning amendments made to user data 222 or any of various consumable records 224. The operational records 226 may also include other information related to the control and operation of the system server 200, including statistical, logging, licensing, and historical information.

In one embodiment, graphical views 228 are provided at the server 200 which are pushed to the health tracking device 110 for display thereat of various screen arrangements, as shown in FIG. 1. The graphical views 228 may also include graphical content configured for display on the user interface 210 of the system server 200.

While the system server 200 has been explained in the foregoing embodiment as housing the health tracking program 218 and the various records and databases in the memory 206, it will be recognized that in other embodiments these components may be retained in other one or more remote locations in communication with the health tracking system 100. For example, in at least one embodiment, the consumable records 224 may be data retained by a database separate from the system server 200. Alternatively, the consumable records 224 or certain fields of the consumable records 224 are received from a third party database. In such embodiments, the health tracking application may utilize any number of application programming interfaces (APIs) to access the data in the third party databases and incorporate such information for use in the health tracking application 218, without local storage thereof or utilizing only temporary storage. Accordingly, it will be recognized that the description of the system server 200 of FIG. 2 is but one exemplary embodiment of a data processing system that may be utilized by the health tracking system 100.

A computer program product implementing an embodiment disclosed herein may therefore comprise one or more computer-readable storage media storing computer instructions executable by a processor to provide an embodiment of a system or perform an embodiment of a method disclosed herein. Computer instructions (e.g., the health tracking application 218 including the dietary goals engine 230) may be provided by lines of code in any of various languages as will be recognized by those of ordinary skill in the art. A "non-transitory computer-readable medium" may be any type of data storage medium that may store computer instructions, including, but not limited to a memory card, ROM, RAM, write-capable memories, read-only memories, hard drives, discs, flash memory, or any of various other computer-readable medium. While the dietary goals engine 230 has been described herein as being provided on the memory 206 of the system server 200, it will be recognized that in at least one alternative embodiment, the dietary goals engine may be provided on the health tracking device 110.

Health Tracking Devices

With reference again to FIG. 1, the health tracking devices 110 may be provided in any of various forms. Examples of a health tracking devices 110 configured for use with the health tracking system 100 include a smartphone 110A, a laptop computer 110B, and a desktop computer 110C, as shown in FIG. 1, as well as various other electronic devices. Accordingly, it will be recognized that the health tracking devices 110 may comprise portable electronic devices such as the smartphone 110A or the laptop computer 110B, or stationary electronic devices such as the desktop computer 110C. Other examples of health tracking devices include, handheld or tablet computers, smart watches, portable media players, other wearable devices, or any of various other health tracking devices configured to receive entry of consumables (not shown) and/or comprising sensors to obtain health related data.

In one embodiment, data obtained at one device 110 may be provided to other devices 110 associated to the same user. For example, data entered at the smart phone 110A may be provided to the desktop computer 110C and/or the laptop computer 110B for storage thereat. Alternatively, the data may be stored at a single network storage apparatus (not shown) having a dedicated portion of storage for records relating to the user and accessible by all of the user's devices 110.

Figure 3:
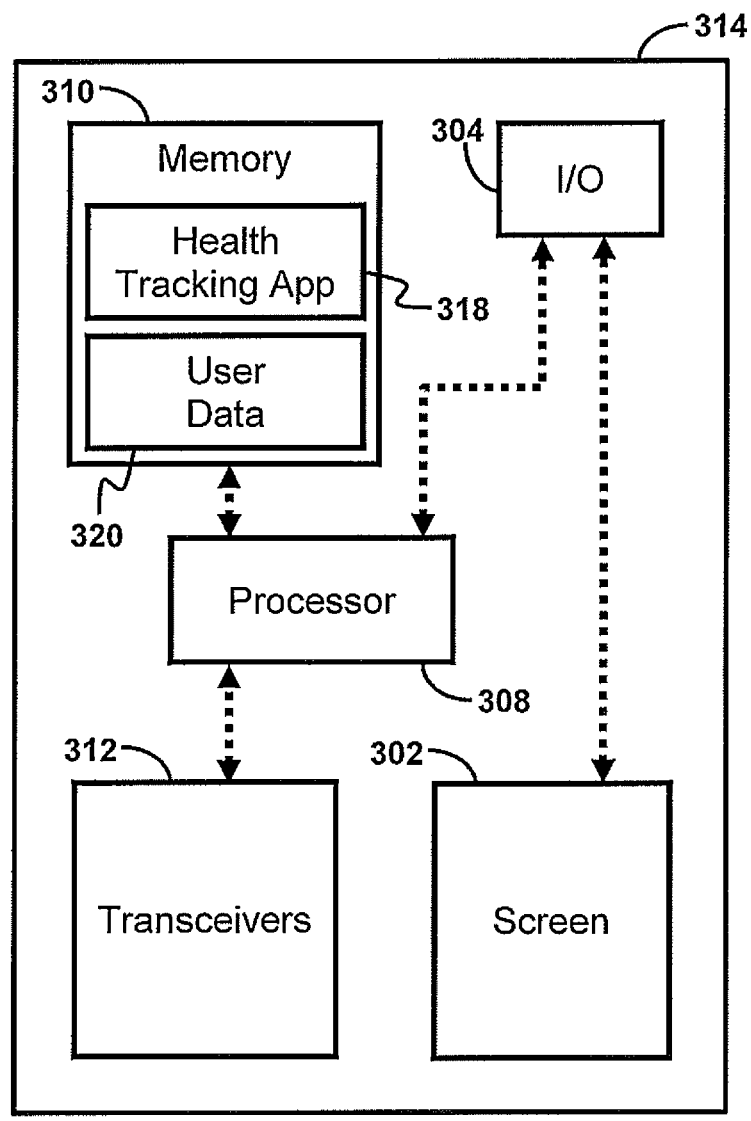
FIG. 3 shows a block diagram illustrating an exemplary system server or data processing system of the health tracking system of FIG. 1.

With reference now to FIG. 3, in at least one embodiment the health tracking device 110 comprises a smartphone 110A. The smartphone 110A includes a display screen 302, an input/output (I/O) interface 304, a processor 308, a memory 310, and one or more transceivers 312. The smartphone 110A also includes a protective outer shell or housing 314 designed to retain and protect the electronic components positioned within the housing 414. The smartphone 110A also includes a battery (not shown) configured to power the display screen 302, processor 308, transceivers 312 and various other the electronic components within the smartphone 110A.

The display screen 302 of the smartphone 110A may be an LED screen or any of various other screens appropriate for the personal electronic device. The I/O interface 304 of the smartphone 110A includes software and hardware configured to facilitate communications with the user. The I/O interface 304 is in communication with the display screen 302 and is configured to visually display graphics, text, and other data to the user via the display screen 302. As will be recognized by those of ordinary skill in the art, the components of the health tracking device 110 may vary depending on the type of display device used. Alternative health tracking devices, such as the laptop 110B and the desktop 110C, may include much of the same functionality and components as the smartphone 110A shown in FIG. 3 and/or may include others not listed.

The processor 308 of the smartphone 110A may be any of various processors as will be recognized by those of ordinary skill in the art. The processor 308 is in communication with the I/O interface 304, the memory 310, and the transceivers 312, and is configured to deliver data to and receive data from each of these components. The memory 310 is configured to store information, including data and instructions for execution by the processor 308. It will be recognized by those of ordinary skill in the art that a "processor" includes any hardware system, hardware mechanism or hardware component that processes data, signals or other information. A processor may include a system with a central processing unit, multiple processing units, dedicated circuitry for achieving functionality, or other systems.

The transceivers 312 may be any of various devices configured for communication with other electronic devices, including the ability to send communication signals and receive communication signals. The transceivers 312 may include different types of transceivers configured to communicate with different networks and systems. Such transceivers are well known and will be recognized by those of ordinary skill in the art. In some embodiments, the transceivers 312 include at least one transceiver configured to allow the smartphone 110A to perform wireless communications with the cell towers 115 of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In some embodiments, the transceivers 312 include at least one transceiver configured to allow the smartphone 110A to communicate with any of various local area networks using Wi-Fi, Bluetooth® or any of various other communications schemes.

The memory 310 includes both program instructions and data. For example, the memory 310 may include program instructions for a graphical user interface configured to provide a client-side health tracking application 318. As noted previously, in at least one embodiment, the health tracking engine includes a dietary goals engine, similar to the network-side dietary goals engine 230 discussed above. With respect to data, the memory 310 may be configured to store certain user data 320, including user profile data such as e.g., user gender, height, weight, user identifier, password, etc. Additionally, user data such as activity and other health related data (e.g., data collected from one or more sensors and/or manually entered) may be stored as user data 320 in the memory 310. The processor 308 is configured to read the program instructions from the memory 310 and execute the program instructions to provide the health tracking application 318 to the user for the purpose of performing health and fitness related tasks for the user, including displaying, modifying, and analyzing the user data 320.

In at least one embodiment, the user data 320 includes a plurality of consumable records which serves as a log of consumables that have been consumed by the user for the purpose of caloric and nutritional tracking. That is to say, the client-side health tracking application 318 is configured to display consumable records and enable the user to select consumable records (from a plurality of records accessed via the network 120), those items that correspond to consumables that he or she has consumed are stored at the client-side for the purpose of logging the consumables in this embodiment. In at least one alternative embodiment, such log may be stored remote from the health tracking device and/or only kept at the health tracking device for a transitory period.

The memory 310 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Alternatively, or in addition, the software (such as e.g., the client side health tracking program 318) may be downloaded from a network location, such as via the Internet.

Method of Providing Meal Guidelines

Methods for operating the health tracking system 100 are described below. In the description of the methods, statements that a method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 204 of the system server 200 and/or the processor 308 of the smartphone 110A can above can be such a controller or processor. Alternatively, the controller can be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Figure 4:
FIG. 4 shows a logical flow diagram illustrating an exemplary method of providing meal guidelines for a user in accordance with one embodiment of the present disclosure.
Figure 4:
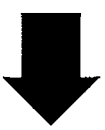
Figure 4:
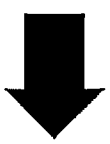

FIG. 4 shows a method 400 of providing meal guidelines for a user of the health tracking system 100. As shown in step 410, the method includes receiving user data from a health tracking device 110 associated with the user. The user data includes at least one long-term dietary goal for the user. The at least one long-term dietary goal is selected or otherwise defined by the user using an associated health tracking device 110. The defined long-term dietary goal may, in one embodiment, be further transmitted from the health tracking device 110 to the system server 200. The system server 200 in this embodiment receives the long-term dietary goal and saves it in the database 220 as user data (e.g., as part of the user profiles 232).

The long-term dietary goal defined by the user may be related to any of various dietary objectives, such as weight loss, weight gain, macronutrient intake, or general healthy lifestyle goals. Furthermore, the long-term dietary goal may be associated with a particular period of time or may be ongoing. If the long-term dietary goal is associated with a period of time, it will be at least one day or longer (e.g., a week, month, year, etc.). One example of a long-term dietary goal that is associated with a particular period of time is for a user lose twenty (20) pounds within twenty weeks. Another example of a long-term dietary goal associated with a particular period of time is to gain seven (7) pounds in two weeks. Alternatively, if a long-term dietary goal is not associated with a particular period of time, that goal is ongoing. One example of an ongoing long-term dietary goal is for the user to limit daily sugar intake to twenty-two (22) grams per day. Another example is for the user to limit calorie intake to one thousand six hundred (1600) calories per day. Yet another example of an ongoing long-term dietary goal may be for the user to maintain a "healthy diet". The system may define a "healthy diet" goal to be one that meets recommend daily allowances (USRDA) established by the U.S. Food and Drug Administration (FDA) for any of various macronutrients.

After a long-term dietary goal is received from the user in step 410, the method 400 continues in step 420 by generating short term dietary goals for the user based at least in part on the received long-term dietary goal. In one embodiment, the short term goals may comprise daily goals. The daily dietary goals are generated by the dietary goals engine 230 which evaluates the user data 222, if needed, and determines a set of recommended actions that will allow the user to achieve the long-term dietary goal. Different user data 222 may be evaluated depending on the long-term goal defined by the user. Accordingly, if the long-term goal of a user is a weight-loss goal (e.g., 20 lbs. in 20 weeks), the user profile data such as gender, height, weight, age, and a general activity level may be evaluated to determine a specific daily calorie intake required for the user to meet the weight loss goal. On the other hand, if the long-term goal of a user is a specific macronutrient intake goal defined by the user (e.g., 25 grams of sugar per day), no evaluation of user data 222 may be required to generate the daily dietary goals, as the goal itself defines the desired daily dietary goals. In a further embodiment, the daily dietary goals generated by the health tracking system 100 are stored as dietary goals 238 in the user data 222 of the database 220. However, in at least one alternative embodiment, the generated guidelines are stored elsewhere in the database 220, such as included with the profile data 232.

As an example of how the dietary goals engine 230 generates daily dietary goals, consider a particular user having a long-term dietary goal to lose twenty (20) pounds in twenty (20) weeks. The profile data for the user indicates that the user is a twenty-five (25) year-old, five foot ten inch (5'10"), two hundred pound (200 lbs.) male with a sedentary lifestyle. By evaluating the profile data associated with this user, it may be determined that the user will maintain his current weight by consuming two thousand (2000) calories per day, but the user will lose a pound a week by consuming only one-thousand five hundred (1500) calories per day. This determination may be made using any of various means, such as look-up tables or various algorithms. After this determination is made, the method generates daily dietary goals for the user based on the user's defined long-term dietary goal to lose twenty (20) pounds in twenty (20) weeks. In this case, the daily dietary goals may recommend a daily calorie limit or maximum for the user of one thousand five hundred (1500) calories per day. In at least one embodiment, the daily dietary goals may be daily calorie range instead of a daily calorie maximum (e.g., 1400-1600 calories). In at least one embodiment, in addition to a recommending a total daily calorie limit, the dietary goals engine 230 is further configured to recommend daily calorie limits that are further focused based on the source of calories or macronutrients (e.g., 35% carbohydrates, 35% protein, 25% fat, 5% sugars).

In the foregoing example, the daily dietary goals generated by the dietary goals engine 230 were the same for each day of the week. However, in at least one embodiment, the user may define his or her long-term goal in a manner that allows for some flexibility between different days of the week. For example, consider the same user discussed in the previous example with a long-term goal to lose twenty pounds in twenty weeks. This user may also indicate that he wishes to consume a significantly larger number of calories on Friday, Saturday and Sunday, such that calorie consumption on these days is more consistent with maintaining his current weight (i.e., 2000 calories per day). In this case, the method may generate daily dietary goals that allow the user to consume 2000 calories per day on Friday-Sunday, but further limit calorie consumption on Monday-Thursday to 1125 per day. In this manner, the user will consume the same total number of calories for the week as he would consume on the 1500 calorie per day pace (i.e., 1500×7=10,500), but the additional calorie restrictions on Monday-Thursday allow for splurging on Friday-Sunday (i.e., (1125×4)+(2000×3)=10,500).

In the foregoing examples, the health tracking system 100 assumes that the user maintains the same generally sedentary activity level. However, in at least one embodiment, the health tracking system 100 may monitor activity of the user as recorded in the activity logs 236 of the database 220, and allow for additional calorie consumption on days of increased activity (or less calorie consumption following days of limited activity). For example, if the user in the foregoing example works out for an hour on a given day and spends an additional 800 calories, the dietary goals for that day may be modified to increase the user's recommended calorie intake by 800 additional calories (e.g., from 1500 to 2300). As another example, if at the end of a particular day it is determined that a user did not log a minimum number of steps (e.g., 3000 for the day) or activity in order to maintain the activity level on which the calculation was based, the system may further restrict the recommended calorie intake on the following day in order to compensate for a low activity level on a previous day (e.g., 100 less calories recommended for the following day).

With continued reference to FIG. 4, in step 430 the health tracking system 100 is further configured to obtain at least one meal goal for the user. Meal goals are sub-goals based on the daily dietary goals for the user. Meal goals are configured to assist the user by splitting the daily dietary goals into a number of smaller meal goals such that achieving each of the meal goals will also allow the user to meet the daily dietary goals. Meal goals may be defined in various ways, but are generally defined as some sub-portion of the daily dietary goals provided by the system 100. Therefore, meal goals may be associated with actual meals (e.g., breakfast, lunch, dinner, brunch, etc.), snacks, or some portion of a day (e.g., morning, afternoon, evening, etc.).

In one embodiment, the meal goals are generated by the health tracking system 100 such as by assigning roughly 30% of the total available calories, macronutrients, etc. to each of breakfast, lunch and dinner, and 10% of the total to snacks. The user may be provided with an interface whereby he/she may modify the default meal goal settings. Alternatively, meal goals may be provided specifically defined by the user (e.g., by changing the defaults or otherwise entering specific values for one or more meal goals). In at least one embodiment, meal goals are defined as a percentage of a daily total. For example, one meal goal may be for the user to consume 30% of his recommended daily calorie intake at breakfast, and another meal goal may be for the user to consume 40% of recommended daily calorie intake for dinner. However, in at least one alternative embodiment, meal goals are specifically defined by the user as specific nutrient values instead of percentages (e.g., the user may input specific numerical amounts for one or more meals, such as 300 calories for breakfast, 600 calories for lunch, etc.). In any event, the system is generally configured to prevent the user from defining meal goals that are inconsistent with the daily dietary goals. For example, the user may not define meal goals such that the total calories for the day exceeds the daily calorie limit, or such that the aggregate percentage for all meal goals is different than one hundred percent (100%). If the user defines meal goals that violate the daily dietary goals, the user is prevented from saving such meal goals.

In another variant, the user may set meal goals for individual days as well as a number of days. For example, the user may set Monday-Friday goals lower in order to have higher goals on Saturday and Sunday.

In at least one embodiment, additional meal goals may be automatically generated by the system based on one or more meal goals provided by the user. For example, if the user provides a meal goal of 30% for breakfast, and 30% for lunch, but fails to provide any meal goal for dinner or snacks, the system may automatically define a meal goal of 40% for dinner and 0% for snacks (or any other alternative such as 30% for dinner and 10% for snacks). As another example, if the user provides a meal goal of 300 calories for breakfast, and 500 calories for dinner, but fails to provide any meal goal for lunch or snacks even though the daily calorie limit is 1500 calories, the system may automatically define a meal goal of 500 calories for lunch and 200 calories for snacks (i.e., 300+500+500+200=1500). Accordingly, it will recognized that even if only one meal goal is provided by the user, the system may be configured to automatically complete additional meal goals. Similar logic may be applied across a number of days, e.g., to ensure the total for a determined short term goal (e.g., a week) is met when the user enters specific goals for certain days.

Although though the system 100 is configured to automatically complete missing or null meal goals, a zero entry for a particular meal goal is acceptable. In particular, a zero entry for a meal goal indicates that the user will skip that particular meal (e.g., some users tend to skip breakfast on a daily basis).

It will be recognized that meal goals may be automatically defined by the health tracking system or may be manually input by the user. For example, the health tracking system 100 may be configured to automatically define meal goals as some default percentage for each meal (e.g., 30% breakfast, 30% lunch, 30% dinner, 10% snacks). However, in at least one embodiment, the user may be provided with the ability to reconfigure the meal goals from the default value to a new value (e.g., 10% breakfast, 35% lunch, 45% dinner, 10% snacks). Moreover, in at least one embodiment, the default meal goals are automatically configured by the system based on the user's historical consumption data. For example, by reviewing the consumable logs 234, it may be determined that a particular user typically consumes 17% of daily calories for breakfast, 42% of daily calories for lunch, 35% of daily calories for dinner, and 6% of daily calories for snacks. This determination may be made in any of various ways, but may be calculated as average daily values for all consumable logs 234 of the user (the average being a mean, mode, median, or other normalized value). Based on the historical data, the health tracking system 100 may automatically define meal goals for the user to match or otherwise reflect the historical data (e.g., the meal goals may be the average daily values for each meal). While these meal goals based on historical consumption data may be automatically defined for the user, in various embodiments the user may be provided with the ability to manually review and adjust the meal goals to meet a desired consumption pattern. For example, although the user's historical consumption data indicates that the user typically consumes 50% of daily consumed calories for lunch, the user may wish to reduce future calorie consumption at lunch and only consume 40% of daily calories at lunch. Accordingly, a user input may provide the user with the opportunity to adjust any automatically defined meal goals.

In step 440 of FIG. 4, meal guidelines or goals for the user are generated by the dietary goals engine 230. The meal guidelines are based on the meal goals obtained for the user and are configured to provide the user with additional definition or recommendations on meeting the meal goals. For example, the meal guidelines may provide the user with a specific number of calories or macronutrient amount that will allow the user to achieve the meal goal (e.g., "500 calories", "10 g of fat," etc.). As another example, the meal guidelines may include one or more recommended food items or other consumables that will allow the user to achieve the meal goal (e.g., "Chipotle® Bean Burrito," or "Mary's Mediterranean pasta recipe," etc.). Meal guidelines are generated by applying the defined meal goal to the daily dietary goals and arriving at a calculation or recommendation based on the defined meal goal. Thus, if a meal goal is defined as a percentage of the daily dietary goal (e.g., 30% for breakfast), the dietary goals engine 230 simply calculates a value for the defined percentage of the daily dietary goal and generates the calculated value as the meal guideline (e.g., 30% of 1500 calories=450 calories; or 30% of 1400-1600 calories=420-480). Similarly, if a meal goal is already a defined value (e.g., 300 calories for breakfast), the generated meal guidelines may be the same as the defined meal goal value (e.g., 300 calories for breakfast). However, in at least some embodiments described in further detail below, the meal guidelines are recommended meals, recipes, or other food records in the consumable records 224 that will allow the user to achieve the defined meal goal.

Exemplary Meal Goals and Guidelines

Figure 5:
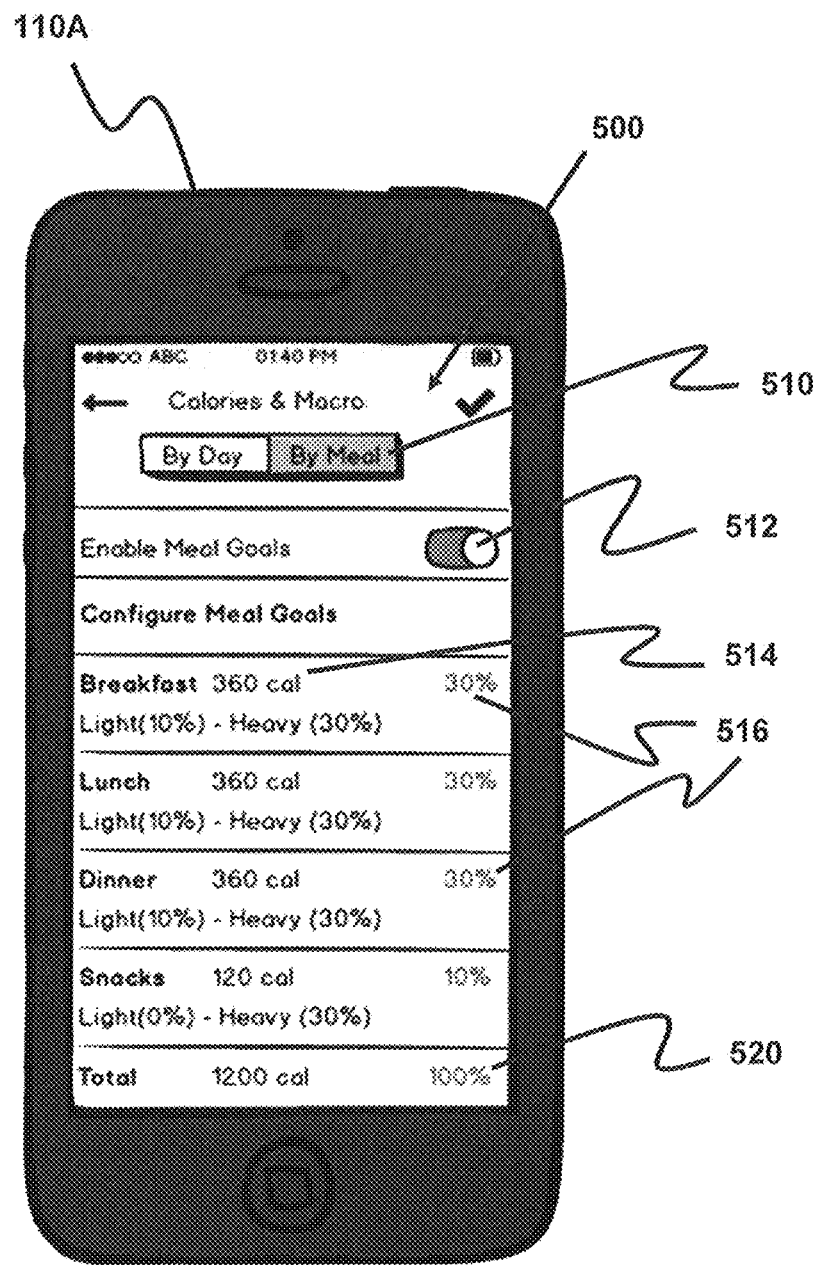
FIG. 5 shows a representation of an exemplary user interface displaying a meal goal configuration screen in accordance with one embodiment of the present disclosure.

With reference now to FIG. 5, an exemplary display screen 500 of the health tracking application 318 is shown on a health tracking device in the form of a smartphone 110A. The screen 500 includes the title "Calories & Macros" and is configured to provide the user with an interface to define sub-goals based on the one or more generated daily dietary goals for the user. As noted previously, the daily dietary goals are based on the user's long term goals (e.g., if the goal is to lose ten pounds in ten weeks, the daily dietary goals provide a daily goal that will allow the user to achieve the stated goal of losing ten pounds within ten weeks). The sub-goals are intended to assist the user in consistently meeting the daily dietary goals and thereby achieving the defined long-term goal. The sub-goals may be meal goals or details for daily goals, both of which provide further resolution for the daily dietary goals. The screen 500 includes a day/meal selector 510 that allows the user to define the sub-goals as either meal goals (i.e., by selecting the "By Meal" option) or detailed daily goals (i.e., by selecting either the "By Day" option).

In FIG. 5, the user has elected to define meal goals by selecting the "By Meal" option on the day/meal selector 510. With the "By Meal" option selected, the user is presented with the meal goals toggle switch 512. If the meal goals toggle switch 512 is "off," the user is prevented from entering any meal goals, and additional screens of the health tracking application 318 may hide data related to meal goals. However, if the meal goals toggle switch 512 is moved to "on" (as shown in FIG. 5), the user is provided with the opportunity to define meal goals, and data related to meal goals may be presented to the user on additional screens of the health tracking application 318 (as described further below with reference to FIG. 7).

With continued reference to FIG. 5, the user is presented with a daily dietary goal 520 at the bottom of the screen 500 to assist the user in determining his or her meal goals. Upon viewing the daily dietary goal 520, the user is in position to better define the desired meal goals. In the exemplary embodiment of FIG. 5, the daily dietary goal 520 provides a total calorie intake of 1200 calories for the day. The user may view and use this information when deciding on appropriate meal goals.

The screen 500 further includes a plurality of meal goal prompts 516 that allow the user to configure meal goals. In the embodiment of FIG. 5, the meal goal prompts 516 are provided along the right side of the screen 500 in association with each listed meal (i.e., breakfast, lunch, dinner, and snacks). The meal goal prompts 516 allow the user to enter a meal goal as a percentage of the daily dietary goal 520. The percentage entered by the user at each of the meal goal prompts 516 is a percentage amount that is less than or equal to 100%.

After the user enters a percentage goal at one of the meal goal prompts 516, the system generates an associated meal guideline 514. The meal guideline is configured to provide the user with even more definition of what he or she should consume for a meal in order to meet the stated meal goal. As noted previously, the meal guideline may take any number of different forms, but in the embodiment of FIG. 5, the meal guideline is a calorie limit for a particular meal. The meal guideline 514 is automatically calculated based on the meal goal entered by the user and the daily dietary goal 520. For example, if the user enters "30%" as the meal goal at the meal goal prompt 516, the health tracking application automatically calculates that 360 calories is 30% of the daily dietary goal (i.e., 0.3×1200=360) and provides this calculation as the meal guideline 514. In the example of FIG. 5, the user has entered meal goals of 30% for each of breakfast, lunch and dinner, and 10% for snacks. Accordingly, the system generates meal guidelines of 360 calories for each of breakfast, lunch and dinner (i.e., 0.3×1200=360) and 120 calories for snacks (i.e., 0.1×1200=120).

While meal goals have been described herein as being defined by a percentage of the daily dietary goal, it will be recognized that meal goals may also be defined differently. For example, in at least one embodiment, a meal goal may be defined as a specific count (e.g., a calorie count), weight (e.g., grams of protein), volume (e g, milliliters of water), or other value associated with a specific meal. Alternatively, meal goals may be defined graphically by the user without the need for the user to input a specific percentage value. For example, the user may move a line on a bar or manipulate a pie chart to indicate the desired of distribution of calories for each meal based on the total calories available from the daily dietary goal. As yet another example, the meal goals may be defined by the user simply indicating which meals of the day should be heavier or lighter. In any event, the system 100 automatically generates meal guidelines based on the meal goals and the daily dietary goals. While FIG. 5 shows the meal guidelines as a specific number of calories for a particular meal, it will be appreciated that the meal guidelines may be provided in other forms, as discussed previously, and as illustrated in further detail below with reference to FIG. 9.

Figure 6:
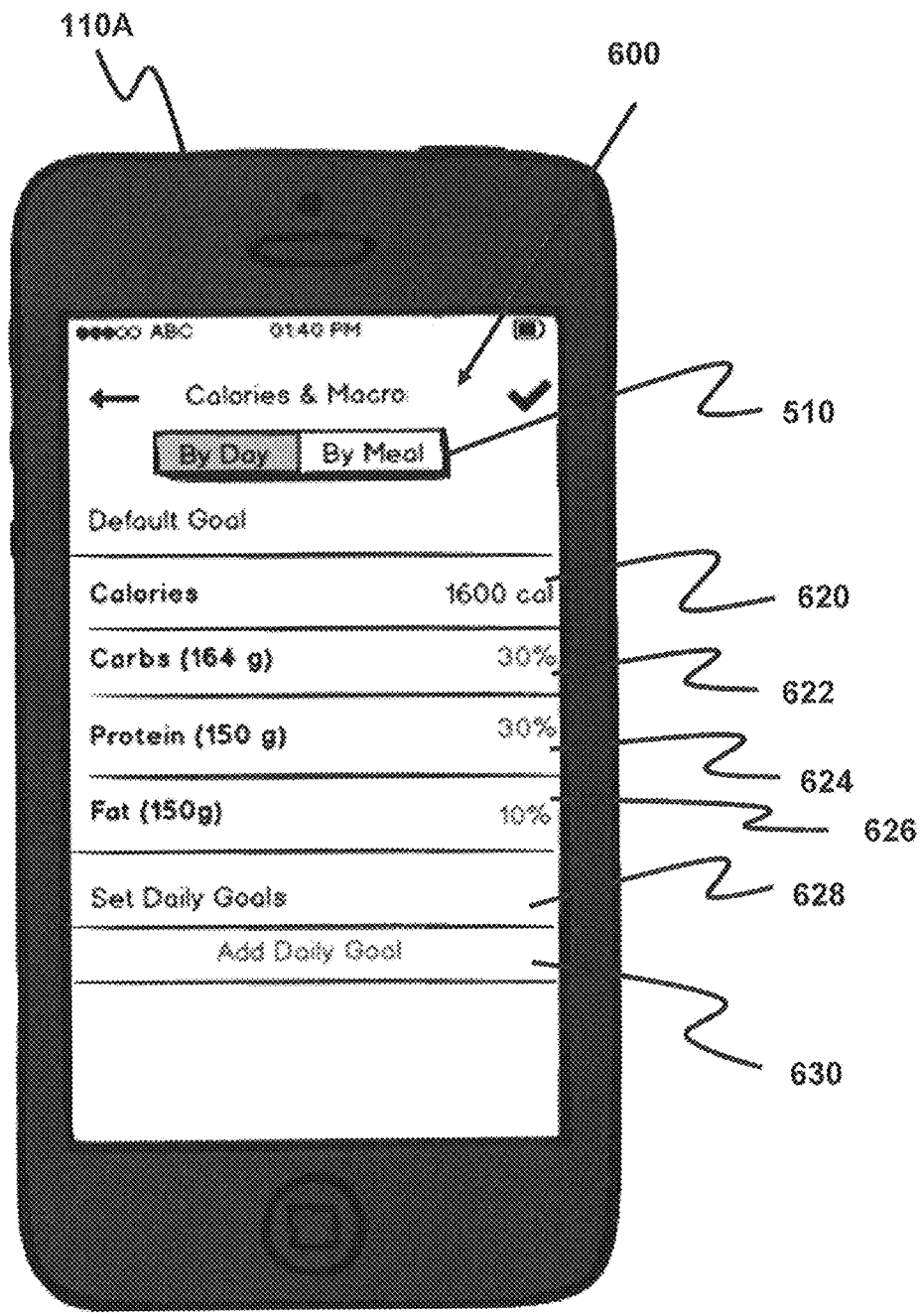
FIG. 6 shows a representation of an exemplary user interface displaying a daily goal details configuration screen in accordance with one embodiment of the present disclosure.

The day/meal selector 510 allows the user to further define the sub-goals to include daily goal details, and not just meal goals. FIG. 6 shows an exemplary screen 600 of the health tracking device 110 wherein the user has further defined daily goal details. As shown in FIG. 6, the user has selected the "By Day" option on the day/meal selector 510, and the daily dietary goal 620 for the user is presented on the screen 600 along with a number of daily goal details in the form of macronutrient details 622, 624, 626. In the example of FIG. 6, the daily dietary goal 620 indicates that the recommended calorie intake for the day is 1600 calories. The macronutrient details include a breakdown of calorie sources for the day, including carbohydrate detail 622, protein detail 624, and fat detail 626. The user has indicated that the daily goal details include obtaining 30% of calories from carbohydrates, 30% of calories from protein, and 10% of calories from fat. Based upon these daily goal details, the system provides guidelines recommending that the user should strive for a daily intake of carbohydrates of about 164 g (i.e., 30%×1600 calories×0.34 g/cal=164 g), a daily intake of protein of about 150 g, and a daily intake of fat of about 15.0 g. Calories may also come from additional sources (e.g., sugars), but those sources are not recognized in the exemplary screen 600 of FIG. 6, and in this embodiment, there is no requirement for the percentages of the daily goals to total 100% (or for the aggregate quantities of the daily goals to be equal to the daily dietary goals). However, the user may include macronutrients or calorie sources (e.g., sugars, minerals, etc.) in the list of daily goals by selecting the "Add Daily Goal" option 630.

Figure 7:
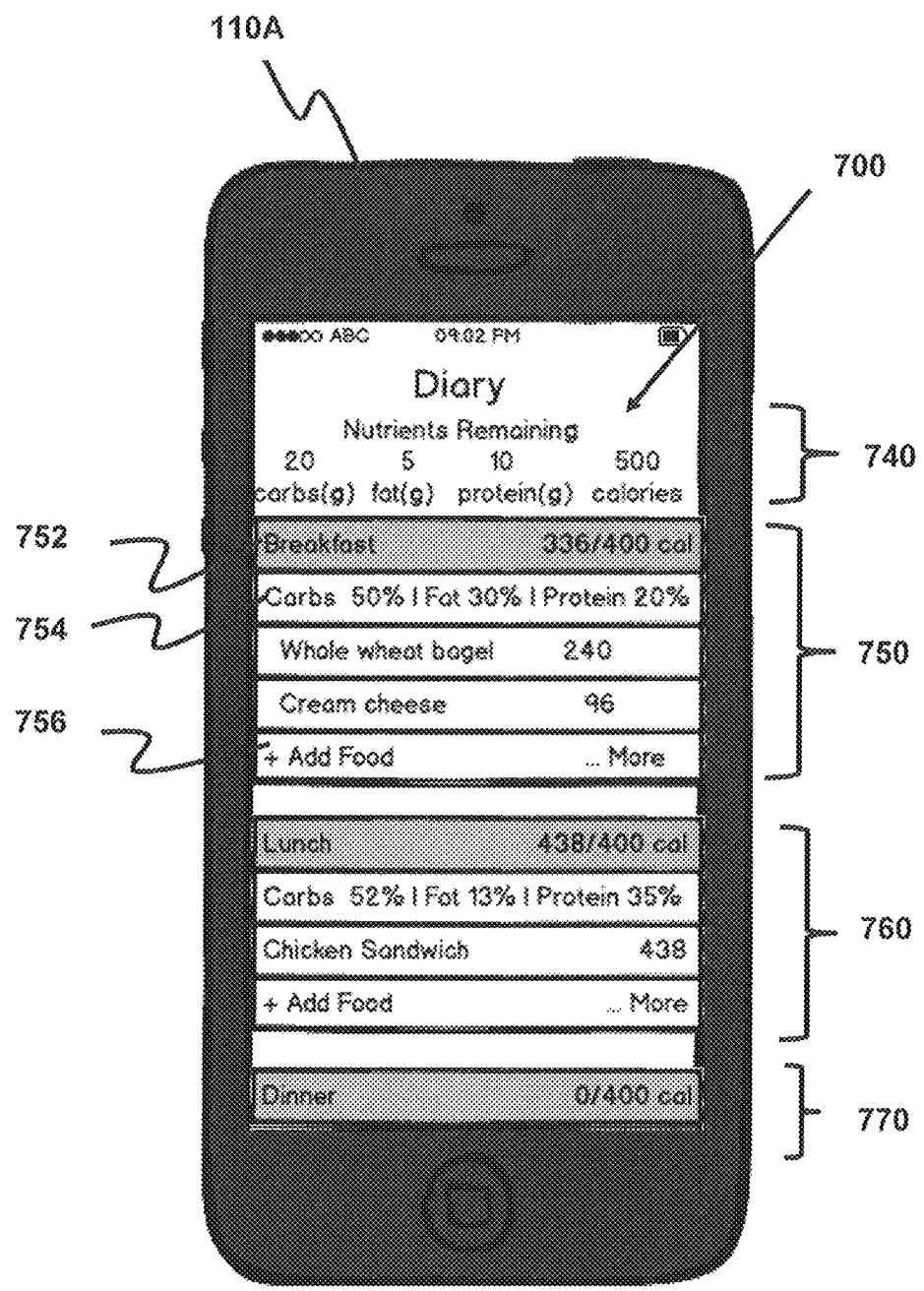
FIG. 7 shows a representation of an exemplary user interface displaying a consumable diary/log screen with static meal goals in accordance with one embodiment of the present disclosure.

When meal goals or other sub-goals are entered by the user, those sub-goals may provide additional functionality for the health tracking application 318. FIG. 7 shows an exemplary diary screen 700 of the health tracking application 318 on the smartphone 110A. The diary screen 700 provides the user with the ability to log foods consumed by the user for the day. In particular, the user log foods and other consumables by selecting the appropriate consumable records 224 from the database 220 using the health tracking application 318, and entering the selected records as consumption data. If meal goals were also entered by the user, the diary screen 700 provides the user with the associated progress toward achieving the daily dietary goal and the associated meal goals.

In the example of FIG. 7, the user has entered foods consumed for breakfast in block 750, and the user has entered foods consumed for lunch in block 760. No foods have been logged for dinner in block 770. As shown in block 750, the user logged two consumable records for breakfast. In particular, the user logged a first consumable record with the descriptive string "whole wheat bagel" and a second consumable record with the descriptive string "cream cheese." The consumable records 224 selected by the user indicate that the whole wheat bagel provided nutritional content of 240 calories and the cream cheese provided nutritional content of 96 calories. As a result, the user logged a total of 336 calories for breakfast. This total is shown in line 752 along with the meal goal defined by the user of limiting breakfast to 400 total calories. In particular, line 752 shows the ratio of calories logged to the meal goal: "336/400". Accordingly, by quickly reviewing the breakfast block 750, the user can quickly determine that the meal goal for breakfast was achieved. Line 754 provides a breakdown of the macronutrient content for the foods logged for breakfast, including carbohydrates, fat and protein (i.e., 50% of the breakfast meal was carbohydrates, 30% was fat, and 20% was protein). If the user desired to view specific nutritional data for any of the food records listed, the user may click on the descriptive string and view the additional macronutrient data (e.g., carbohydrate, fat, protein, sugars, vitamins, minerals, etc.). In the event the user realizes that additional foods should be logged for breakfast, the user can select the "Add Food" option 756.

Similarly, as shown in block 760, the user logged a chicken sandwich for lunch. The consumable records 224 selected by the user indicate that the chicken sandwich provided 438 calories and the cream cheese provided 96 calories. As a result, the user logged a total of 438 calories for lunch. This total is slightly greater than the meal goal defined by the user of limiting lunch to 400 total calories. In particular, block 760 shows the ratio of calories logged to the meal goal: "438/400". Accordingly, by quickly reviewing the lunch block 760, the user can quickly determine that the meal goal for breakfast was not achieved, but the user only exceeded the meal goal by 38 calories. Block 760 also provides a breakdown of the macronutrient content for the foods logged, including carbohydrates, fat and protein (i.e., 52% of the lunch meal was carbohydrates, 13% was fat, and 35% was protein). In the event the user realizes that additional foods should be logged for lunch, the user can select the "Add Food" option in block 760.

Block 740 of FIG. 7 shows the nutrients remaining for the user to meet the daily dietary goal. In this case, the user's daily dietary goal was 1274 calories/day, and the user has already consumed 774 calories (i.e., 338 breakfast calories+438 lunch calories=774 calories). This leaves 500 calories remaining for the user to meet the daily dietary goal (i.e., 1274−774=500). Similarly, because the user has defined detailed daily goals for carbohydrates, fat and protein, block 740 also provides remaining carbohydrates (i.e., 20 g), fat (i.e., 5 g), and protein (10 g) that will allow the user to meet the detailed daily goals.

Dynamic Meal Guidelines

In at least one embodiment, the health tracking system 100 is configured to dynamically adjust one or more meal guidelines for the user based on consumable records logged by the user. In particular, the health tracking system 100 may be configured to define a first meal guideline for a first meal (e.g., breakfast) and a second meal guideline for a second meal (e.g., lunch), and then, after the user logs consumption data for the first meal, revise or otherwise update the second meal guidelines. Similar logic applies to the daily goals across multiple days, where a first day being over or under a short term goal (such as a weekly goal), dynamically impacts the goals for the remainder of the days in that week.

Figure 8:
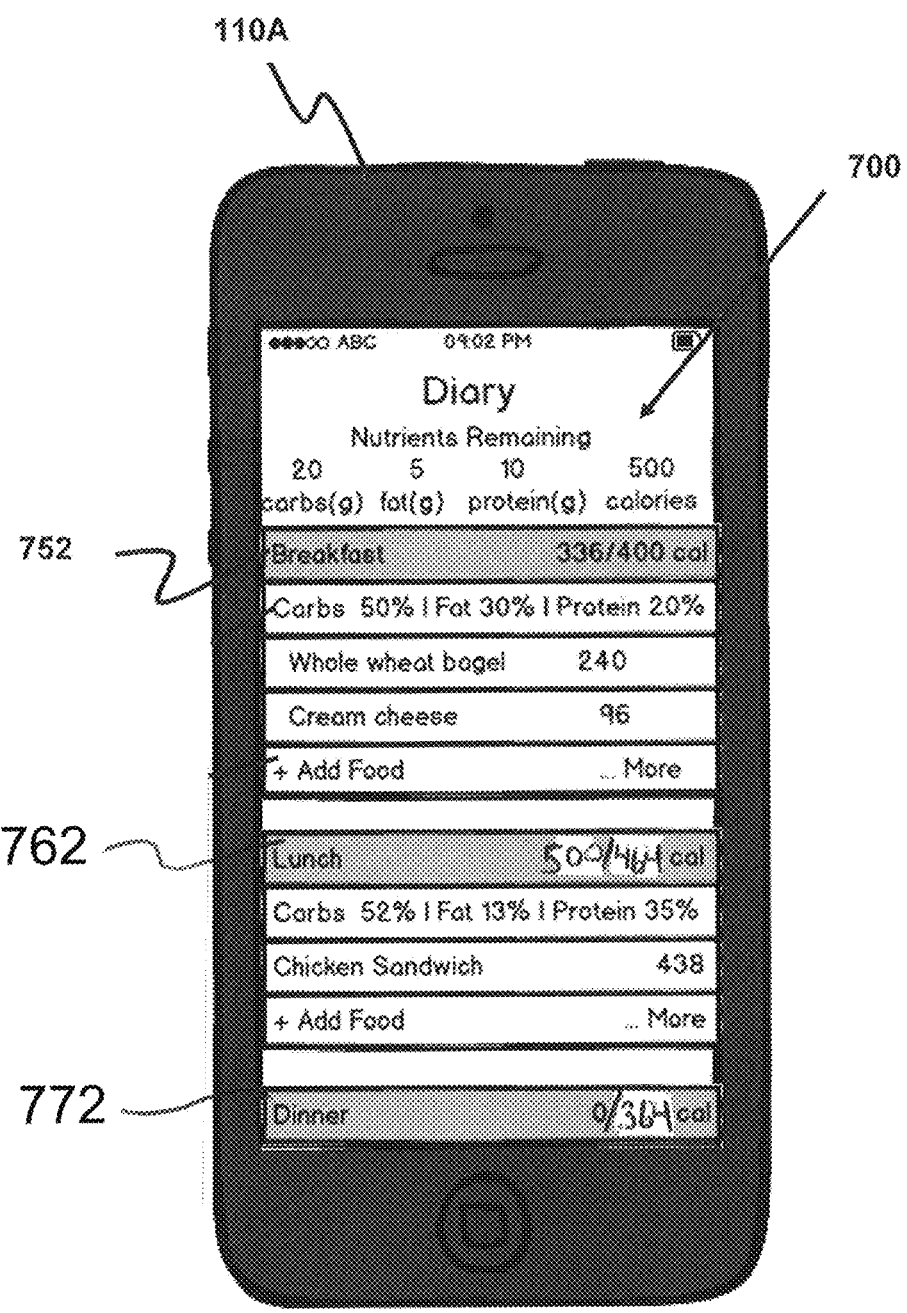
FIG. 8 shows a representation of an exemplary user interface displaying a consumable diary/log screen with dynamic meal goals in accordance with one embodiment of the present disclosure.

FIG. 8 shows an alternative embodiment of the diary screen 700 of FIG. 7 implementing dynamic meal guidelines. In particular, at the start of the day, the meal guidelines for the user indicated that the user should consume a maximum of 400 calories for each of breakfast, lunch, and dinner. As shown in line 752, the consumption data logged by the user for breakfast was 64 calories short of the 400 calorie meal goal for breakfast (i.e., 400−336=64). This extra 64 calories was then transferred to the lunch meal guideline, and the 400 calorie lunch meal guideline was updated to include the extra 64 calories from breakfast (i.e., 400+64=464), as shown in line 762.

As shown in line 762, the consumption data logged by the user for lunch was 36 calories in excess of the updated 400 calorie lunch meal guideline (i.e., 500−464=36). This excess of 36 calories was then transferred to the dinner meal guideline, and the original meal guideline for dinner was reduced by the excess 36 calories from lunch, as shown in line 772 (i.e., 400−36=364 calories). In this manner, the dynamic meal guidelines are configured to assist the user by providing direction for the user that will allow the user to meet the daily goal (i.e., 1200 calories), regardless of whether previous meal goals for the day were met by the user.

While FIG. 8 shows an exemplary embodiment of dynamic meal guidelines wherein meal guidelines are adjusted meal-by-meal, other embodiments of dynamic meal guidelines are possible. For example, instead of transferring excessive or reduced calorie consumption for one meal to the immediately following meal goal, reduced or excessive calories may be split amongst all of the remaining meals. Thus, in the example of FIG. 8, the excess of 64 calories from breakfast could be immediately transferred to both the lunch and dinner meal guidelines with half of the calories (i.e., 32 calories) transferred to the lunch meal guideline and half of the calories (i.e., 32 calories) transferred to the meal guideline. As yet another example, instead of transferring excessive or reduced calorie consumption for one meal to the next meal goal of the day, the excessive or reduced calorie consumption may be transferred to one or more meal guidelines for the following day (e.g., an excess of 100 calories from Monday may be transferred to breakfast on Tuesday or split evenly amongst all meal goals for Tuesday). In this manner, it will be recognized that the health tracking system 100 may be configured to dynamically adjust one or more meal guidelines for the user to future meal guidelines based on consumption data logged by the user.

Recommended Meals as Meal Guidelines

As noted previously, the recommended meal guidelines may be provided in various forms, including, for example, maximum calories, a calorie range, target macronutrients, etc. Furthermore, in at least one embodiment, the recommended meal guidelines are provided as meal options that may be either purchased or prepared by the user (e.g., an item from a restaurant menu, or a recipe in the consumable records).

Figure 9:
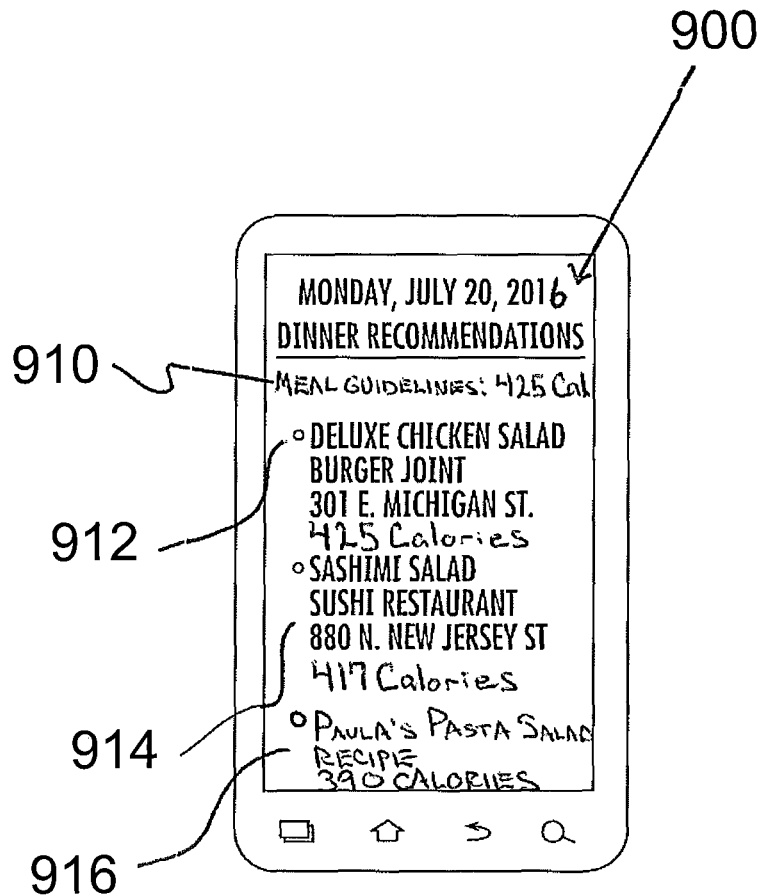
FIG. 9 shows a representation of an exemplary user interface displaying a meal guideline screen with meal options in accordance with one embodiment of the present disclosure.

With reference to FIG. 9, a meal guideline screen 900 is shown. The meal guideline screen includes a maximum calorie line 910, which indicates the maximum number of calories that the user may consume and meet the meal guidelines for dinner on Jul. 20, 2016. In this case, the maximum calories that the user may consume to meet the meal guidelines is 425 calories. The meal guideline screen further includes two meal options 912 and 914 in the form of menu items from local restaurants capable of meeting the meal guidelines in line 910. These meal options 912 and 914 are based on the user's present proximity to any of various restaurants and the associated menu items in the consumable records 224 of the database 220. The user may purchase either of the meal options 912 or 914 and log those menu items as consumption data in order to meet the dinner guideline listed in line 910 of FIG. 9. In the embodiment of FIG. 9, the meal guideline screen 900 also provides at least one additional meal option in the form of a recipe 916 from the consumable records 224 that may be prepared by the user in order to meet the dinner guideline listed in line 910 of FIG. 9. The meal options 912, 914 and 916 may be generated by the system based on any of various criterion, including (i) the recommended meal meeting the meal guideline (e.g., macronutrients, calories, etc.), (ii) the user's proximity to a restaurant offering the meal recommendation, and (iii) past meals logged by the user (i.e., the meal recommendation is a meal previously logged by the user some predetermined number of times), as well as various other criterion. If the user selects any of the meal options 912, 914, or 916 in FIG. 9, the selected meal option will be logged as consumable data for the user.

The methods discussed herein may be accomplished with the assistance of a computer program, such as the network and/or client side health tracking programs described above. The above described system and method solves a technological problem common in industry practice related to effective and efficient presentation of serving size data. Moreover, the above-described system and method improves the functioning of the computer/device by allowing health data to be effectively communicated to the user along with a graphical user interface that presents food item serving size selection options to the user.

Portions of the system and methods described herein may be implemented using one or more programs or suitable software code, such as the network and/or client-side health tracking applications, described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, infrared, or semiconductor system, apparatus, system, device, or computer memory. The computer readable medium may include multiple computer readable media storing computer executable instructions, such as in a distributed system or instructions stored across an array. A "non-transient computer-readable medium" may be any type of data storage medium that can store computer instructions, including, but not limited to the memory devices discussed above.

The above described system and method solves a technological problem common in industry practice of assisting users of evaluating user goals and adjusting meal guidelines based on consumption data received from the user. Moreover, the above-described system and method improves the functioning of the computer device by causing enabling users to easily define meal goals in a health tracking system and providing meal guidelines associated therewith. In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method for providing a dietary plan, comprising:
providing at least one database comprising a plurality of consumable item data records entered by users of a health tracking system, each data record comprising one or more respective nutritional values;
receiving from a graphical user interface (GUI) of a health tracking device a long-term nutrition or weight-related goal of a user, the health tracking device including a global positioning system (GPS) sensor;
utilizing user profile information to identify a daily caloric value necessary to achieve the long-term nutrition or weight-related goal;
automatically generating daily meal goals for the user by apportioning the daily caloric value across a plurality of individual meals associated with each day such that a relative portion of the daily caloric value is apportioned to each of the plurality of individual meals;
enabling the user to dynamically adjust, via an indicia on the GUI, the relative portion of the daily caloric value apportioned to one of the plurality of individual meals such that the adjusted relative portion is greater than or less than the previous relative portion for at least one of the daily meal goals and, in response thereto, automatically changing the daily value apportioned to another individual meal when the daily value apportioned to the one individual meal is dynamically adjusted;
receiving data relating to one or more consumed items associated to a first one of the plurality of individual meals, the data comprising at least a caloric value thereof;
updating the portion of the daily caloric value apportioned to subsequent ones of the plurality of individual meals based on a difference between the caloric values of the received data and the daily caloric value;
determining a user location based on data from the GPS sensor;
searching the at least one database and identifying individual ones of the plurality of consumable item data records based at least in part on said user location and said consumable item data records containing respective values that meet the daily caloric value apportioned to one of the plurality of individual meals;
presenting descriptive information relating to the identified individual ones of the plurality of consumable item data records to the user on the GUI of the health tracking device;
determining that the user location has changed to an updated user location based on data from the GPS sensor; and removing the descriptive information related to the identified individual ones of the plurality of recipe records from the GUI based on the updated user location.

2. The method of claim 1, wherein enabling the user to dynamically adjust further comprises enabling the user to dynamically adjust one or more macronutrient component parts of the portion of the daily caloric value apportioned to each of the plurality of individual meals.

3. The method of claim 1, wherein an amount of the daily caloric value apportioned to each of the individual meals associated with each day is based at least in part on historical consumption data of the user.

4. The method of claim 1, wherein the user profile information comprises at least (i) data obtained from the user including one or more of: height, weight, gender, and age, and (ii) data derived from historical activity data relating to the user.

5. The method of claim 1 wherein the plurality of individual meals include at least breakfast, lunch and dinner.

\* \* \* \* \*